United States Patent
Mizutani et al.

(10) Patent No.: US 7,150,912 B2
(45) Date of Patent: Dec. 19, 2006

(54) INTER-LABIUM PRODUCT AND SURFACE-SIDE SHEET CAPABLE OF DISINTEGRATION IN WATER FOR THE INTER-LABIUM PRODUCT

(75) Inventors: Satoshi Mizutani, Mitoyo-gun (JP); Koichi Yamaki, Mitoyo-gun (JP); Yuki Noda, Mitoyo-gun (JP); Megumi Tokumoto, Mitoyo-gun (JP); Kazuya Okada, Mitoyo-gun (JP)

(73) Assignee: Uni-Charm Corporation, Shikokuchuo (JP)

( * ) Notice: Subject to any disclaimer, the term of this patent is extended or adjusted under 35 U.S.C. 154(b) by 0 days.

(21) Appl. No.: 11/081,011

(22) Filed: Mar. 15, 2005

(65) Prior Publication Data

US 2005/0221071 A1    Oct. 6, 2005

Related U.S. Application Data

(63) Continuation of application No. PCT/JP03/10566, filed on Aug. 21, 2003.

(30) Foreign Application Priority Data

Sep. 17, 2002    (JP)    ............................... 2002-270684

(51) Int. Cl.
*D02G 3/00*    (2006.01)

(52) U.S. Cl. ...................... 428/401; 428/359; 428/364; 604/359; 604/367; 604/380; 604/383; 604/375

(58) Field of Classification Search ................ 604/359, 604/367, 370, 375, 383, 378, 380, 385; 428/359, 428/401, 364
See application file for complete search history.

(56) References Cited

U.S. PATENT DOCUMENTS 3,983,873 A  *  10/1976  Hirschman ............. 604/385.17

(Continued)

FOREIGN PATENT DOCUMENTS

JP    09-078419 A1    3/1997

(Continued)

*Primary Examiner*—Merrick Dixon
(74) *Attorney, Agent, or Firm*—Darby & Darby

(57) ABSTRACT

An inter-labium product capable of disintegration in water, fitted to the inter-labium part; and a surface-side sheet for inter-labium product that simultaneously realizes comfortability at wearing of the inter-labium product and capability of water disintegration such that the inter-labium product is disintegrated when thrown in flush water of water closet after use. The surface-side sheet for use in an inter-labium product fitted to the inter-labium part is comprised of hydrophilic fibers composed of single fibers and fibril fibers having fuzzes branched from the surface thereof, wherein at least some of the branched fuzzes link the single fibers and the fibril fibers to each other. Thus, not only can the wet tensile strength be increased but also inter-fibrous bonds are slowly decomposed in the presence of a large amount of water to thereby enable disposal of the inter-labium product in a flush toilet. Furthermore, since no resin is used, the inter-labium product is free from resin leaching to thereby avoid problems, such as itching and skin roughness, caused by the resin leaching.

14 Claims, 6 Drawing Sheets

U.S. PATENT DOCUMENTS

| | | | | |
|---|---|---|---|---|
| 4,095,542 A | * | 6/1978 | Hirschman | 112/475.06 |
| 4,142,476 A | * | 3/1979 | Hirschman | 112/475.08 |
| 4,175,561 A | * | 11/1979 | Hirschman | 604/385.17 |
| 4,196,562 A | * | 4/1980 | Hirschman | 53/450 |
| 4,595,392 A | * | 6/1986 | Johnson et al. | 604/385.17 |
| 6,649,807 B1 | * | 11/2003 | Mizutani | 604/367 |
| 6,765,124 B1 | * | 7/2004 | Wada et al. | 604/359 |

FOREIGN PATENT DOCUMENTS

| | | |
|---|---|---|
| JP | 09-285486 A1 | 11/1997 |
| JP | 10-151153 A1 | 6/1998 |
| JP | 2000-501322 A1 | 2/2000 |
| JP | 2000-512886 A1 | 10/2000 |
| JP | 2001-079037 A1 | 3/2001 |
| JP | 2001-172850 A1 | 6/2001 |
| JP | 2001-172851 A1 | 6/2001 |
| JP | 2001-288657 A1 | 10/2001 |
| JP | 2001-288658 A1 | 10/2001 |
| JP | 2002-061060 A1 | 2/2002 |
| JP | 2002-078733 A1 | 3/2002 |
| JP | 2002-513638 A1 | 5/2002 |
| JP | 2002-263137 A1 | 9/2002 |

* cited by examiner

INTER-LABIUM PRODUCT AND SURFACE-SIDE SHEET CAPABLE OF DISINTEGRATION IN WATER FOR THE INTER-LABIUM PRODUCT

CROSS-REFERENCE TO RELATED APPLICATIONS

This application is a Continuation of International Application No. PCT/JP2003/010566 filed Aug. 21, 2003, which application published in Japanese on Apr. 1, 2004 as WO 2004/026204 A1 under PCT Article 21 (2). The International Application PCT/JP2003/010566 is based upon and claims the benefit of priority from Japanese Patent application No. 2002-270684 filed on Sep. 17, 2002, the entire contents of which is incorporated herein by reference.

FIELD OF THE INVENTION

The present invention relates to an interlabial product that degrades with water and that can be discarded as it is by throwing into the discharge water of the flush lavatory, after having been worn between labia and absorbed body fluid such as menstrual blood or others discharged from interlabia, and a water degradable surface side sheet for the interlabial product.

RELATED ART

Conventionally, interlabial products to be worn between labia have been known. As an interlabial product, a water degradable interlabial product to be dissipated by a large amount of discharge water of the toilet and degraded into small fragments to a degree not to hold the original shape, when thrown into the toilet, has been developed. The water degradable interlabial pad can be discarded by throwing into a so-called flush lavatory, because this will not fill the piping of the toilet.

For instance, the interlabial pad disclosed in the JP-A-2000-501322 can be cited as such a water degradable interlabial pad. That is, the interlabial pad disclosed in the JP-A-2000-501322 has a liquid permeable surface side sheet facing to the inner wall of the wearer's labia and a first fiber like assemble and a wet highly resisting resin such as a glyoxalic polyacrylamide resin or others on the liquid permeable surface side sheet. This wet highly resisting resin is water degradable and dissipated in the water as the linkage between materials is untied in a large amount of water or the water flow; however, the material doesn't degrade in the moisture of a prescribed amount while worn. Therefore, the material doesn't remain in the labia, and the growth of bacteria can be prevented.

However, elusion components may elude from the wet highly resisting resin that composes the interlabial pad, so that the body is chemically stimulated by these elusion components and itchy and skin roughness might be caused.

By the way, the surface side sheet of the interlabial product and the inner wall of labia may come to rub each other when the interlabial product is worn, and the wearer might have an unpleasant feeling. In order to solve this inconvenience, an absorbent interlabial tool is disclosed, for instance, in the JP-A-2000-512886. That is, the absorbent interlabial tool disclosed in the JP-A-2000-512886 contains a polysiloxane type emollient composition at least partially in the body contact face. As a result, the interlabial tool can reduce unpleasantness, by decreasing the friction between the body and the absorbent interlabial tool.

However, for such an interlabial pad, the inner wall of labia and the body contact face of the interlabial product might become slippery. Therefore, the interlabial product may cause dislocation while worn, and drop out from interlabia. In addition, a viscous element of the polysiloxane type emollient composition contained in the surface side sheet of the interlabial product may remain on the inner wall of labia or the pudenda and cause an unpleasant feeling. In addition, components may elude from the polysiloxane type emollient composition as to stimulate the body chemically and cause itchy and skin roughness.

Moreover, to achieve the dropout prevention from interlabia and the decrease of the sense of discomfort while worn, the interlabial product is designed in a compact size compared with the napkin and the liner. Hence, because the size is compact, the surface side sheet, that is the body side of the interlabial product, is easily covered with menstrual blood. Therefore, if the interlabial product after use cannot be thrown into the toilet as it is, the interlabial product after use shall be disposed by the hand. At this time, if the interlabial product is folded with its surface side sheet face inside as in case of napkin or liner, the menstrual blood turns up to adhere to the finger, and this is not only insanitary, but also takes time very much. Moreover, they try to dispose of it by using the individual wrapping body where the unused interlabial product has been stored, without folding the surface side sheet face of the interlabial product after use, an unused interlabial product shall be worn, after having wrapped the used interlabial product will in the individual wrapping body. Therefore, the unused interlabial product taken out from the individual wrapping body after having it opened shall be put somewhere temporarily, and at this time, an inconvenience that the unused interlabial product is polluted is caused, if the place has not been cleaned.

SUMMARY OF THE INVENTION

The present invention has been made in view of the aforementioned inconveniences and has an object to offer the interlabial product that have both comfort while wearing and water degradability allowing it to degrade with water rapidly when it is thrown in the flush lavatory after use, and the surface side sheet for this interlabial product.

In order to solve the aforementioned inconveniences, the Inventors came to find the following characteristics, and to complete the present invention to solve the problem like the above-mentioned. That is, a fibril fiber having with a lot of minute branch hairs from the surface of the fiber, was used at least for a part of the fiber that composes the surface side sheet and adjacent fibers were bridged mutually with branch hairs. As a result, fibers that compose the surface side sheet are connected mutually one the other, to maintain without deforming the original shape of the sheet, in a wet state where body fluid such as menstrual blood has been absorbed. On the other hand, it will resolve to a degree not to keep the original shape, uniting the mutual binding of fibers, when it comes into contact with a large amount of water.

More concretely, the present invention offers the one like the following.

(1) A water degradable surface side sheet for an interlabial product to be worn between labia, comprising a hydrophilic fiber having a filament and a fibril fiber which has branch hairs branching from its surface, wherein at least a part of the branch hairs make bridges between the filament and the fibril fiber.

Here, the filament mean fibers that any physical post-processing such as fibrillation is not exerted. Moreover, the fibril fiber means a fiber having a lot of branch hairs formed by beating.

According to the invention of (1), the water degradable surface side sheet has a filament which is single fiber and a fibril fiber having branch hairs branching from their surface. As a result, at least a part of branch hairs which are contained in the fibril fiber bind the filament and the fibril fiber which is disposed adjacent each other, so that bridge structures are formed. Hence, the water degradable surface side sheet doesn't easily get untied and degraded, even in a wet state where body fluid such as menstrual blood has been absorbed. On the other hand, in a large amount of water such as the discharge water of the toilet, the bridge structures are gradually resolved, so that the water degradable surface side sheet comes to be degraded.

Therefore, the interlabial product can be thrown after used as it is into the toilet. When the wearer disposes of the interlabial product, the wearer only has to detach the interlabial product from between labia by hand, or by the pressure of her urine. That is, the wearer needs not to dispose of the used interlabial product separately, and the hand of the wearer is sanitary as the hand does not get dirty.

Moreover, water degradability, which decomposes the mutual connection of fibers with a large amount of water and increases the strength in the wet state, is achieved by binding filament and fibril fiber through branch hairs of the fibril fiber. Therefore, because the resin including the elusion component is not used, neither itchy nor the skin roughness, etc. are caused. Moreover, shagginess and so on are not caused easily, because the binding among fibers is strong, even if the water degradable surface side sheet rubs against the inner wall of labia.

(2) The water degradable surface side sheet for the interlabial product wherein the fibril fiber is blended 3 to 30 weight % of the hydrophilic fiber.

According to the invention of (2), the water degradable surface side sheet does not only lose flexibility but also get degraded easily even in the wet state where body fluid such as menstrual blood has been absorbed. The elongation degree can be improved, and moreover, the bridge structures of branch hairs are gradually resolved, and the original shape as the sheet is not maintained, against a large amount of water such as the discharge water of the toilet. Note that the bridge structures are broken easily and durability decreases when the fibril fiber is fewer than 3 weight % of the hydrophilic fiber, because the bridge structures are too little, and the elongation degree in the wet state doesn't improve. On the other hand, the water degradable surface side sheet may lose flexibility as the bridge structures are too much, when the fibril fiber is more than 30 weight % of the hydrophilic fiber.

(3) The water degradable surface side sheet for the interlabial product, wherein maximum elongation degree on most is higher than maximum elongation degree on dry.

According to the invention of (3), as maximum elongation degree in the wet state of the water degradable surface side sheet is made higher than maximum elongation degree in the dry state, the water degradable sheet becomes hard to break even if the tensile strength decreases in the wet state.

(4) The water degradable surface side sheet for the interlabial product, wherein the degree of beating of the branch hairs of the fibril fiber is 100 cc to 400 cc.

According to the invention of (4), as the strength decrease due to the fibrillation of the fiber fibril can be suppressed, the tensile strength and the elongation degree in the wet state where body fluid has been absorbed can be improved, together with the mutual binding of fibers by the bridge structures of the fibril fiber and the filament. The branches of the fibers increase and strength of the fibril fiber decrease because the level of beating is violent when the degree of beating is less than 100 cc. Moreover, when the degree of beating is larger than 400 cc, the number of branch hairs decreases, and the bridge structure of the filament and the fibril fiber decreases, in case of forming a sheet by laminating hydrophilic fibers, and it is likely to break when it becomes wet.

(5) The water degradable surface side sheet for the interlabial product, wherein the fibril fiber is rayon.

The rayon is generated by the wet method or the dry method, and the fiber length can be selected from the range of 1 to 38 mm freely. Therefore, according to the invention of (5), bridge structures having flexibility can be obtained, while uniting the filament and the fibril fiber, because the length of the branch hairs can be made longer, by making the rayon from the fibril fiber thorough beating.

Natural fabrics are generally different in the fiber length and hard, so that it is difficult to form a steady bridge structures, because the length of the branch hair also becomes disparate, event when the natural fabric is fibrillated by beating. On the other hand, the rayon allows selecting the fiber length freely, and has less dispersive than the natural fabrics. In addition, as the rayon is hydrophilic, consequently, and also excellent in compatibility with the body fluid and fitness to the inner wall of labia, it is possible to use the rayon suitably as fibril fiber.

(6) An interlabial product for being worn between labia, comprising a water degradable surface side sheet for being in a face of the labia and a back side sheet arranged on a opposite side of the water degradable surface side sheet (garment side), wherein the water degradable surface side sheet comprising a hydrophilic fiber having a filament and a fibril fiber which has branch hairs branching from its surface, wherein at least a part of the branch hairs make bridges between the filament and the fibril fiber.

According to the invention of (6), the water degradable surface side sheet of the interlabial product comprises a hydrophilic fiber comprising a filament and a fibril fiber with branch hairs branching from its surface. At least a part of branch hairs has a bridge structure which forms a bridge between the filament and the fibril fiber mutually. Hence, the water degradable surface side sheet doesn't easily get untied and degraded, even in a wet state where body fluid such as menstrual blood has been absorbed. Therefore, the interlabial product dose not shift in the wearing position nor fallen off between labia. On the other hand, the bridge structure of the branch hairs is gradually resolved, and the water degradable surface side sheet comes to be degraded, for a large amount of water such as the discharge water of the toilet, the interlabial product is resolved into small fragments.

(7) The interlabial product, wherein a total size in a transverse direction of the surface side sheet in a state, where the interlabial product is folded on a fold line drawn along a longitudinal direction so that the water degradable surface side sheet is exposed to outside, is longer than that of the surface side sheet in a state, where the interlabial product is tabular.

According to the invention of (7), when the interlabial product is folded on a fold line drawn along the longitudinal direction, so that the water degradable surface side sheet is exposed to outside, the total size in the transverse direction of the surface side sheet is longer than that before it is folded. Consequently, the surface side sheet is not pressed by the absorbent body provided inside the interlabial product, even when the interlabial product is folded, and the force to restore the state of the interlabial product before folding, namely the force to open both the end edges of the interlabial product can be controlled. Therefore, this interlabial product doesn't drop out, because it does not expand the end edge of the labia, even if the interlabial product is worn between labia.

Here, the state where the interlabial product is tabular means a state where the interlabial product is open, and the total size in the transverse direction means the size from the one end edge to the other end edge, along the transverse direction of the interlabial product.

Now, the meaning of the fact that the total size in the transverse direction of the surface side sheet in the state where the interlabial product is folded is larger than the size in the transverse direction of the surface side sheet before it is folded shall be described. That is, when the interlabial product is folded in two parts along the longitudinal direction, the size in the transverse direction of the surface side sheet located most outside of the interlabial product is longer than the size in the transverse direction in tabular state before it is fold, by the order of the circumferential length of a half circle having the thickness of the interlabial pad as radius.

Thus, the following methods may be enumerated as a method of lengthening the total size in the transverse direction of the surface side sheet in the two parts-folded state of the interlabial product more than the size in the transverse direction in the tabular shape. For instance, there is a method wherein the total size in the transverse direction of the surface side sheet is enlarged more than the total size in the transverse direction of the back side sheet, and it is joined with the surface side sheet in a state where the surface side sheet is loosened in the transverse direction. Moreover, there is a method of connecting the surface side sheet with this back side sheet, in a state where the back side sheet and the absorbent body are folded in two parts. Moreover, there is a method of making the surface side sheet elongate easily in the transverse direction, and connecting the surface side sheet and the back side sheet in the tabular shape state. At this time, besides the execution of ripple processing along the transverse direction, or the slit processing, of the surface side sheet, the maximum tensile elongation degree in the transverse direction may be set to 100% or more, as the characteristic of the surface side sheet itself. It should be remarked that it is preferable to form the surface side sheet by wet forming spun lace and make the maximum tensile elongation degree in the transverse direction 100% or more by the tendering processing, for connecting with the back side sheet, considering the simplicity of the processing process.

(8) The interlabial product, wherein the back side sheet comprises a hydrophilic fiber including a fibril fiber.

According to the invention of (8), the back side sheet had the hydrophilic fiber including a fibril fiber. As a result, when the interlabial product is thrown in to the toilet from the back side sheet first, the hydrophilic fiber of the back side sheet gets affinity to the water immediately. Therefore, it is possible to discard the interlabial product more surely with the discharge water of the toilet, by preventing it from coming up to the surface of the water.

Moreover, the back side sheet might rub mutually when the interlabial product is worn, and the back side sheet of the interlabial product and the napkin might rub when a napkin is used together with the interlabial product. Even for this case, as the friction drag is decreased by the back side sheet, the body fluid leakage can be prevented due to getting untied of the back side sheet. In addition, the fibril fiber of the hydrophilic fiber can decrease the breakage of the back side sheet further even if the body fluid adheres to the back side sheet and makes it wet.

This back side sheet is the one where a hydrophilic fiber sheet such as tissues is bonded or laminated on a film or the like having hydrolyzed biodegradable resin as raw material, in consideration of the wettability to the water when discarding it into the toilet. Here, the hydrophilic fiber sheet is the one including the fibril fiber such as the rayon and so on. Moreover, polyvinyl alcohol (PVA) film, film wherein one face or/and both faces are made water-repellent with silicon or the like, PVA film wherein silicon is blended, starch film, polylactic acid or polybutylenesuccinate, etc. may be enumerated as the film. Note that, leakage prevention function under wearing and wettability to the discharge water of the toilet when discarding might also be afforded at the same time, by adjusting the water-repellent degree through the execution of water-repellent processing to the hydrophilic fiber by sizing agent and so on. Moreover, as necessary, inorganic pigments may be blended in the back side sheet within the range of 0.1 to 5% for coloring.

Moreover, those similar to the one explained as the surface side sheet, previously, can be used as a hydrophilic fiber sheet including the fibril fiber. That is, more particularly, the hydrophilic fiber sheet is a spun lace nonwoven fabric adjusted to by a specific weight per unit within the range of 20 to 60 $g/m^2$ by blending a necessary amount of fiber in the range of 1 to 38 mm in the fiber length, more preferably in the range of 2 to 20 mm and within the range of 1.1 to 3.3 dtex in fineness. The fibril fiber 3 to 30 weight % and the filament 97 to 70 weight % are desirable as the mixture ratio of the fibril fiber and the filament.

Moreover, the specific weight per unit of the film of the back side sheet adhered to the hydrophilic fiber sheet including the fibril fiber is 19 to 40 $g/m^2$, it is joined by the embossing finish or an adhesive, and the joint rate is desirably in the range of 1 to 30%. Moreover, when it is laminated with a hydrophilic fiber sheet including the fibril fiber, the thickness of the resin to be laminated is desirably in the range of 10 to 40 μm.

(9) The interlabial product, comprising a mini sheet piece for inserting a finger, wherein the mini sheet piece is provided on the back side sheet and includes a fibril fiber.

According to the invention of (9), the mini sheet piece to insert a finger in the garment side of the interlabial product is provided on the garment side of the back side sheet. As a result, as the labia can be pushed open by the rigidity of the finger when the interlabial product is worn between labia, it is possible to install it up to the vestibule bed surely and, as a gap is not created between the vestibule bed or the inner wall of labia and the body side of the interlabial product, the body fluid can be prevented from leaking.

Moreover, as this mini sheet piece includes a fibril fiber, twining of the fiber gets untied in a large amount of water or in the water flow of the toilet, and it is resolved into small fragments. As this mini sheet piece including a fibril fiber, those used for the surface side sheet and the back side sheet above-mentioned can be used.

Note that it is desirable to set the nonwoven fabric side to the garment side, considering wettability to the water when throwing into the toilet and the friction drag of the mini sheet pieces each other, if a laminate sheet bonded with a non-woven fabric that has the fibril fiber is to be used.

(10) The interlabial product is for incontinence.

According to the invention of (10), the interlabial product can be used for an incontinence absorb product. That is ostium vaginae where the blood is discharged and a pee hole where urine is discharged locate between labia, and the interlabial product of the present invention to be used between labia can absorb urine also. Therefore, it can absorb urine around labia, especially around the pee hole and is useful for incontinence, especially for a light incontinence.

(11) The interlabial product for absorbing vaginal discharge.

According to the invention of (11), the interlabial product can be used for absorbing the vaginal discharge. That is the interlabial product is used between labia and can absorb the excretion (vaginal discharge) other than the blood from ostium vaginae. Therefore, the interlabial product can absorb the vaginal discharge in order to decrease the discomfort for the person, and is useful for the user who is not menstruating.

(12) A wrapping having an interlabial product for being worn between labia and a wrapping sheet for enveloping the interlabial product inside, wherein said interlabial product comprises a water degradable surface side sheet for being in a face of the labia and a back side sheet arranged on a opposite side of the degradable surface side sheet (garment side), wherein said water degradable surface side sheet comprising a hydrophilic fiber having a filament and a fibril fiber having branch hairs branching from its surface, wherein at least a part of branch hairs make bridges between said filament and the fibril fiber, and said wrapping sheet includes a fibril fiber.

According to the invention of (12), the twine among fibers, of the sheet for wrapping, gets untied in a large amount of water or in the discharge water of the toilet, and is resolved into small fragments as the sheet for wrapping composing the wrapping body includes a fibril fiber. Therefore, as the wrapping body after unsealing can be thrown into the toilet, the wrapping body can easily be discarded. Moreover, as it is unnecessary to discard the wrapping body after unsealing into a sanitary box, the finger is not smeared dirty, and when a new interlabial product is worn, the interlabial product, the inner wall of labia, and the vulva, and so on are never smeared, and it is therefore sanitary.

In addition, as for the act to discard the interlabial product into the toilet bowl by detaching from between labia with urine pressure of the wearer, the interlabial product can be taken out from the between labia by gripping it via the wrapping body and thrown in the toilet bowl as it is, in case where the wearer has a sanitary aversion, or in case where she can not let the interlabial product detach from between labia, due to the body type of the wearer, even if she opens her inside of the thigh towards the toilet bowl.

The material used for the above-mentioned surface side sheet and the back side sheet can be used for the sheet for wrapping. When a nonwoven fabric composed only of the fiber is used for the sheet for wrapping to decrease the load to the stream of the piping and the septic tank, the maximum elongation degree in the wet state can be improved by including the fibril fiber in the sheet for wrapping. As a result, the wrapping body is opened without damaging the sheet for wrapping and the operativeness is never impaired, even when the wearer washes her hands before wearing the interlabial product and her hands are wet. Moreover, as the barrier function thereof is high, the interlabial product can be treated sanitarily, even if it is wrapped with the sheet for wrapping when discarded, because the density of the sheet for wrapping can be improved. To improve the barrier function further, the water-repellent treatment might be performed with silicon, sizing agent, etc.

(13) Fibril fiber for a water degradable product, comprising branch hairs branching from its surface.

According to the invention of (13), the branch hair of the fibril fiber forms the bridge structure to twine the fiber mutually, and connects mutually fibers that compose the water degradable product. Therefore, the fibers don't easily get untied and the water degradable fiber doesn't degrade while wearing it, even in the wet state where body fluid such as menstrual blood has been absorbed. On the other hand, the bridge structure of the branch hair is gradually resolved, and the water degradable product degrades for a large amount of water such as the discharge water of the toilet.

(14) A method for improving a stability of a hydrophilic fiber soaked in small quantity of water, wherein the hydrophilic fiber comprises a filament and a fibril fiber having branch hairs branching from its surface, comprising the step of; making bridges between the filament and the fibril fiber with at least in a part of the branch hairs.

According to the invention of (14), as the bridge structure is formed by forming bridges between the filament and the fibril fiber each other, the uniting power between fibers can be improved, and the original form can be maintained as the hydrophilic fiber doesn't get untied in the wet state in contact with a small quantity of water.

BRIEF DESCRIPTION OF THE DRAWINGS

FIG. 5A is figure of the examination body, which is used to examine the practicality and to examine the aqueous dispersibility of the above-mentioned interlabial product, seen from the surface side sheet side.

FIG. 5B is figure of the examination body, that was used to examine the practicality and to examine the aqueous dispersibility of the above-mentioned interlabial product, seen from the back side sheet side, and.

DESCRIPTION OF THE PREFERRED EMBODIMENT

Next, one embodiment of the interlabial product of the present invention shall be described referring to figures; however the present invention is not limited to this.

Figure 1:
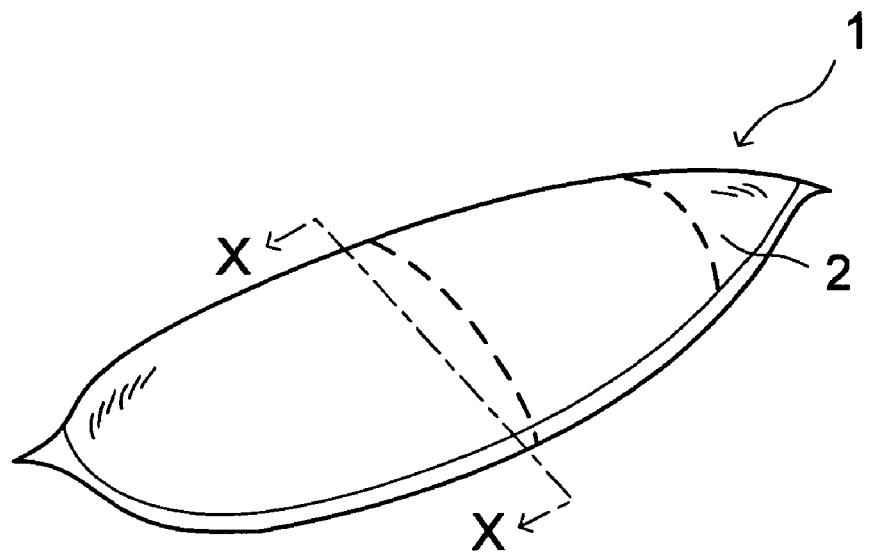
FIG. 1A is a perspective view showing an interlabial product according to an embodiment of the present invention
FIG. 1B is a cross-sectional view along the line X—X of FIG. 1A.
Figure 1:
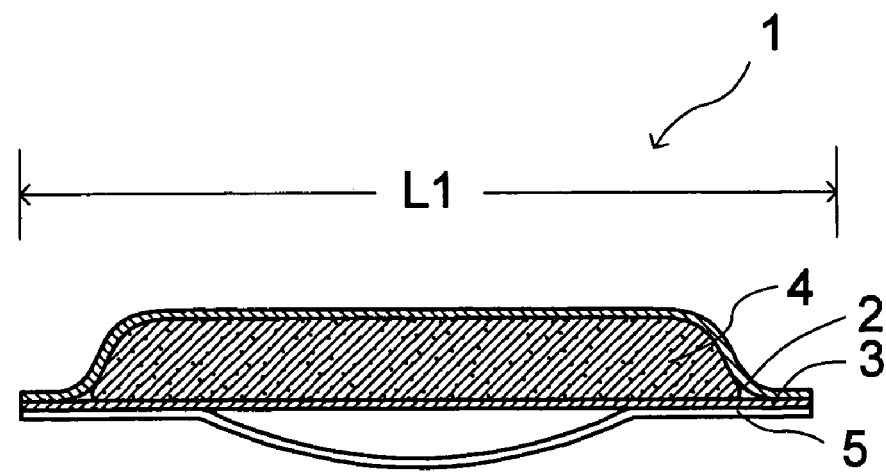

A basic composition of the interlabial product of this embodiment shall be described. FIG. 1A is a perspective figure showing the interlabial product according to this embodiment, and FIG. 1B is a cross-sectional view of FIG.

1A along the line X—X inside in the interlabial product according to this embodiment.

[General Composition of the Interlabial Product]

An interlabial product 1 in this embodiment has an elongated thin shape, and comprises a water permeable surface side sheet facing to an inner wall of labia 2, a water permeable or non-permeable back side sheet 3 facing to the garment, and an absorbent body 4 enveloped in these sheets 2, 3 for absorbing body fluid, as shown in FIG. 1A and FIG. 1B. A mini sheet piece 5 is attached on the garment side of the back side sheet 3, across two side parts extending along the longitudinal direction of the interlabial product 1.

Moreover, the interlabial product 1 is formed within the range of 50 to 130 mm in the length size and 30 to 80 mm in the lateral size, and the thickness is desirably adjusted within the range of 2 to 20 mm, for the fitness with the inner wall of labia, dropout prevention from between the labia, and blocking prevention of the piping of the toilet.

Figure 2:
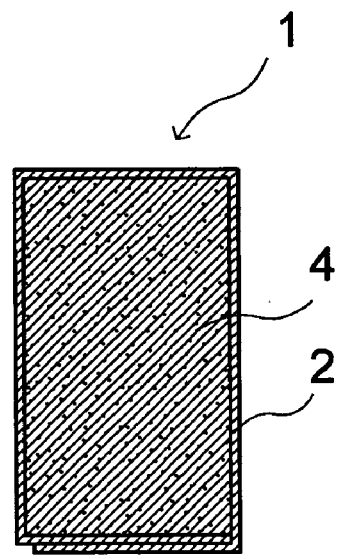
FIG. 2A is a cross-sectional view showing a variant of the above-mentioned interlabial product.
FIG. 2B is a cross-sectional view showing a variant of the above-mentioned interlabial product.
Figure 2:
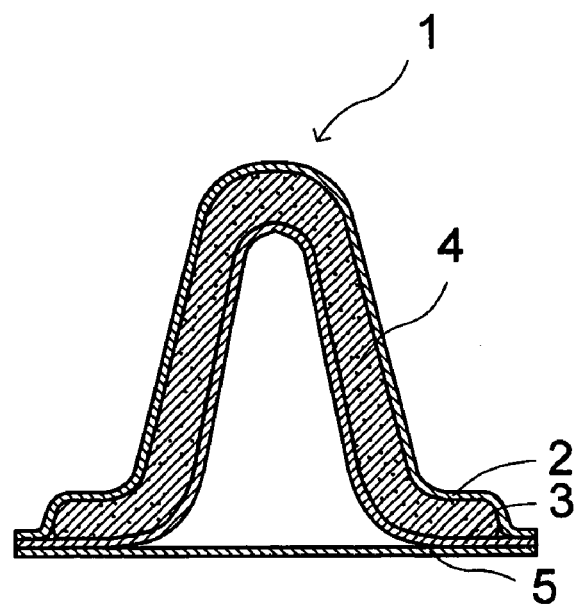

Note that though the interlabial product 1 in this embodiment is plane, it is not especially limited in the present invention provided that the shape can be maintained by placing it between labia, such as the rectangular type, bottle gourd type, droplet type, etc. Moreover, though the cross-sectional view shape of the interlabial product 1 in this embodiment is hog-backed shape, the section shape is not especially limited, provided that the shape that can be maintained by placing it between labia, such as the rectangular one as shown in FIG. 2A, one folded approximately in V as shown in FIG. 2B, and so on.

[Composition Material of the Interlabial Product]

<Surface Side Sheet>

Figure 3:
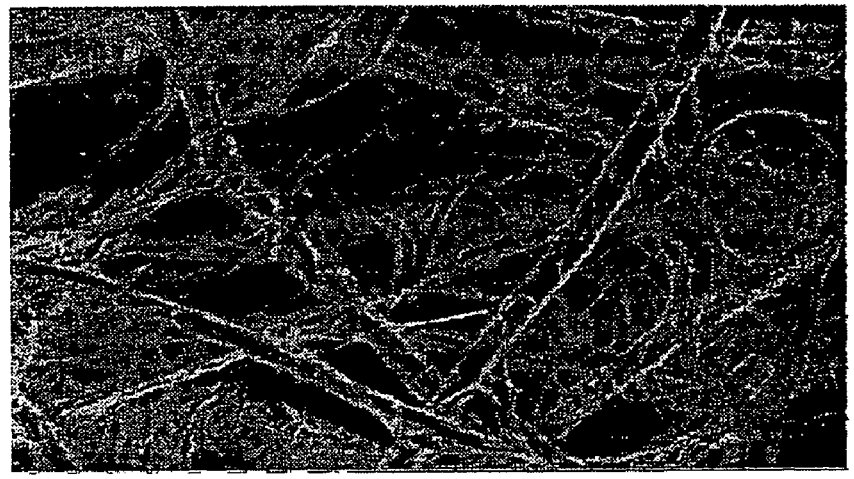
FIG. 3A is a photomicrograph that shows the surface side sheet (fiber blended with fibril fiber) composing the above-mentioned interlabial product.
FIG. 3B is a photomicrograph that shows the binding state of fibers not blended with fibril fiber.
Figure 3:
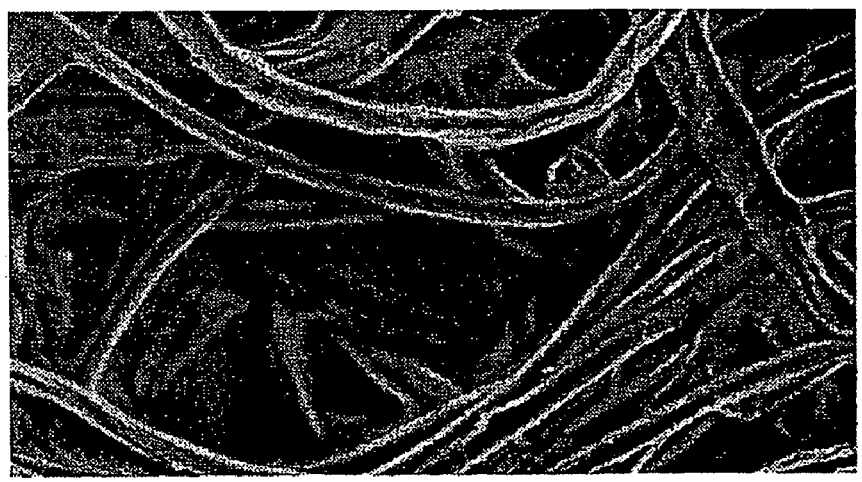

A surface side sheet 2 according to the present invention comprises the hydrophilic fiber composed of filament that is one single fiber and the fibril fiber provided with a lot of branch hairs branching from the surface of the fiber, as shown in FIG. 3A. At least a part of these branch hairs forms a bridge structure for mutually bridging between the filament and the neighboring fibril fiber, and the fibers are mutually connected. Here, the fiber with which the fibril fiber is not blended is shown in FIG. 3B. It can be confirmed that divergent branch hairs are intertwined with the fibers each other and the bridge structure is formed on the surface side sheet 2, by the comparison of FIG. 3A with FIG. 3B.

The surface side sheet 2 is a spun lace nonwoven fabric adjusted to by a specific weight per unit within the range of 20 to 60 g/m$^2$ by blending a necessary amount of fiber in the range of 1 to 38 mm in the fiber length, more preferably in the range of 2 to 20 mm and within the range of 1.1 to 3.3 dtex in fineness. More particularly, the surface side sheet 2 is formed into a fiber laminated body by blending the fibril fiber within the range of 3 to 30 weight % and the filament within the range of 70 to 97 weight %. Moreover, the surface side sheet 2 is produced by intertwining these blended fiber laminated bodies by the high pressure water-flow before drying, and by adjusting the density to 0.08 to 0.20 g/cm$^3$.

The fiber used for this surface side sheet 2 is the one to be biodegraded to gases such as carbon dioxide or methane, water, and biomasses according to the process of nature, in the presence of bacteria including the ray fungi and other microbes, and under the anaerobic or aerobic condition. Concretely, the selection is made as appropriate from biodegradable material that is biodegradable under the same environment, water dispersible material where the fibers are dispersed in fragments so as not to block the piping of the toilet in a large amount of water or the water-flow, and never to pile up in the air diffusion pipe in the septic tank, though the influence is small with the limited amount of moisture in use, and water solubility material that dissolves in a large amount of water or the water-flow, though the influence is small with the limited amount of moisture under wearing. Here, poly lactic acid fiber, polybutylenesuccinate fiber, starch film fiber, carboxymethyl cellulose fiber and so on can be listed as biodegradable material, and these fibers are used alone or two or more in combination.

In addition, those free from elution material, or, free from chemical stimulation, even if elution material eludes, in the wet state under wearing is preferable, in consideration of the chemical stimulation to the wearer.

As for the fiber used for this surface side sheet 2, concretely, semi-synthetic fibers such as regenerated celluloses including rayon and acetate rayon, synthetic fibers such as polypropylene, polyester, polyurethane, polyvinyl alcohol and so on may be enumerated, besides the natural fibers such as wood pulps including softwood pulps, hardwood pulps and so on, hemp, kenaves, linters pulps and so on. The one mainly composed of the rayon that is hydrophilic and that can be freely selected within the range of 1 to 38 mm in the fiber length is much more desirable from the viewpoint of affinity with the menstrual blood and the fitness with the inner wall of labia.

The following compositions are listed, as a concrete composition the of surface side sheet 2. For instance, the hemp fiber is fibrillated within the range of 1 to 38 mm, preferably 2 to 20 mm, and 100 to 400 cc in the degree of beating, preferably 200 to 300 cc. This fibrillated hemp fiber within the range of 3 to 30 weight %, the rayon within the range of 70 to 97 weight %, 1 to 38 mm in the fiber length, preferably 2 to 20 mm, and 1.1 to 3 dtex in the fineness are combined, and laminated at 30 to 45 g/m$^2$ by a specific weight per unit.

A polyvinyl alcohol fiber is fibrillated within the range of 1 to 38 mm, preferably 2 to 20 mm, and 100 to 400 cc in the degree of beating, preferably 200 to 300 cc. This fibrillated polyvinyl alcohol fiber within the range of 3 to 30 weight % and the rayon within the range of 70 to 97 weight %, 1 to 38 mm in the fiber length, preferably 2 to 20 mm, and 1.1 to 3.3 dtex in the fineness are combined, and laminated at 30 to 45 g/m$^2$ by a specific weight per unit.

The rayon is fibrillated in the range of 1 to 38 mm, preferably 2 to 20 mm, and 100 to 400 cc in the degree of beating, preferably 200 to 300 cc. This fibrillated rayon within the range of 3 to 30 weight % and the softwood pulp within the range of 70 to 97 weight %, 1 to 10 mm in the fiber length, substantially 2 to 5 mm, are combined, and laminated at 30 to 45 g/m$^2$ by a specific weight per unit.

Further, wood pulp, linter pulp fiber, or carboxymethyl cellulose fibrillated in the range of 1 to 10 mm, substantially 2 to 5 mm, and 250 to 650 cc in degree of beating, and the rayon of 80 to 99 weight % in the range of 1 to 38 mm in fiber length, preferably 2 to 20 mm, and 1.1 to 3 dtex in the fineness are combined, and laminated at 30 to 45 g/m$^2$ by a specific weight per unit.

Besides, this surface side sheet 2 is formed into melt blown, spun bond, point bond, through air, needle punch, wet paper, wet forming spun lace and so on, solely with the hydrophilic fiber where little hydrophilic surface active agent is adhered or blending the necessary amount. For instance, by using the spun lace method, various fibers alone or blended as necessary are intertwined by the water-flow interlacing treatment, and then the spun lace nonwoven fabric is produced. According to the spun lace method, this water-flow interlacing treatment allows detaching substantially by the water-flow, the surface active agent that adheres to the fiber to prevent the irregularity of specific weight per unit by static electricity when the fiber is untied. Therefore, as the chemical stimulation caused by the above-mentioned surface active agent is decreased, so it is more preferable. Note that, it is more preferable, in this case, to adjust the specific weight per unit within the range of 20 to 60 g/m². The fiber density rises too high when the specific weight per unit is more than 60 g/m² and the fitness with the inner wall of labia is not attained. On the other hand, when the specific weight per unit is fewer than 20 g/m², the required strength under wearing can not be obtained.

The fibril fiber is attained by the formation of branch hairs like the outgrowth of hair in a way to tear the surface of the fiber, by beating of the aforementioned single fiber. This degree of beating is 600 cc or less, more preferably 100 to 400 cc. Besides, it is blended with the fiber that composes the surface side sheet at least at the rate of 2 weight %, and preferably within the range of 3 to 30 weight %. When the fibril fiber is fewer than 2 weight %, it is likely to degrade while wearing it, because the bridge structure is too little and the elongation degree in the wet state doesn't improve. On the other hand, the bridge structure increases too much, when the fibril fiber is more than 30 weight % and a flexible texture of the surface side sheet might be damaged.

It should be noted that as the fibril fiber, the rayon that is hydrophilic and excellent in the affinity with the menstrual blood and the fitness with the inner wall of labia, and moreover, that can be selected freely among those with long fiber length, is suitable. The rayon allows to attain the bridge structure having flexibility while preventing the filament being separated mutually, because the length of the branch hair can be lengthened, when it is fibrillated through beating, as it can be produced by the wet method or the dry method, and the fiber length can freely be selected within the range of 1 to 38 mm.

Here, the rayon produced by the dry method is more preferable, because the molecular arrangement of cellulose is more aligned in one direction than the one produced by the wet method, and easy to split against the power of beating.

The manufacturing method of the fibril fiber by the dry method, for instance, dissolves the pulp to N-methylmorpholine oxide that is an organic solvent, forms a fiber from a nozzle, and volatilizes the solvent. Afterwards, this fiber is cut within the range of 1 to 38 mm, and more preferably within the range of 2 to 20 mm, and further preferably within the range of 2 to 10 mm, and the size is adjusted within the range of 1.1 to 3.3 dtex so that it will have biodegradability and be dispersed in small fragments in a large amount of water or in the discharged flow without maintaining its original shape. Then, the fiber cut in the prescribed length is put into the water and fibrillated by the beating at least by 600 cc or less, and more preferably within the range of 100 to 400 cc. As a result, the fibril fiber will be 10 mm or less in the length of the branch hair, and the branch hair makes up 50 to 100% of the whole.

<Back Side Sheet>

The back side sheet 3 is the one in which a filmy sheet that can prevent the menstrual blood kept in the absorbent body 4 from leaking outside the interlabial product 1 and the hydrophilic fiber sheet including the fibril fiber is bonded. Concretely, a hydrophilic fiber sheet such as tissues is stuck, or laminated on the filmy sheet, in consideration of the wettability to the water when it is discarded in the toilet. Here, this hydrophilic fiber sheet is the one including the fibril fiber such as the fibrilrayon, and so on. As the filmy sheet, the polyvinyl alcohol (PVA) film, the film where the repellent treatment with silicon or the like is executed on one side or/and both sides of the PVA film blended with silicone, the starch film, and the films derived from hydrolyzed biodegradable resins such as polylactic acid or polybutylenesuccinate and so on can be listed. Note that, leakage prevention function under wearing and wettability to the discharge water of the toilet when discarding might also be afforded at the same time, by adjusting the water-repellent degree through the execution of water-repellent processing to the hydrophilic fiber by sizing agent and so on. Moreover, as necessary, inorganic pigments may be blended in the back side sheet 3 within the range of 0.1 to 5% for coloring.

Moreover, those similar to the one explained in the above-mentioned surface side sheet 2 can be used as the hydrophilic fiber sheet including the fibril fiber. That is, more particularly, the hydrophilic fiber sheet is a spun lace nonwoven fabric adjusted to by a specific weight per unit within the range of 20 to 60 g/m² by blending a necessary amount of fiber in the range of 1 to 38 mm in the fiber length, more preferably in the range of 2 to 20 mm and within the range of 1.1 to 3.3 dtex in fineness. The fibril fiber within the range of 3 to 30 weight % and filament within the range of 70 to 97 weight % is preferable as the blending ratio of the fibril fiber and the filament. The specific weight per unit of the film of back side sheet 3 stuck to the hydrophilic fiber sheet including the fibril fiber is 19 to 40 g/m², it is bonded with the embossing finish or the adhesive, and the bonding rate is preferably within the range of 1 to 30%. Moreover, in case of the laminate processing with a hydrophilic fiber sheet including the fibril fiber, the thickness of the resin that is laminated is preferably within the range of 10 to 40 µm.

The laminate processing is, concretely, executed according to the following procedure. First of all, the wet forming spun lace is produced by blending the fibrilrayon whose fiber length is 1 to 38 µm and fiber diameter is 1.1 to 3.3 dtex within the range of 3 to 30 weight %, and the rayon within the range of 70 to 97 weight %, in water where the sizing agent was blended with the fiber weight ratio of 0.05 to 1.0% to the fiber weight, and adjusting the specific weight per unit to 20 to 40 g/m². The PVA resin whose thickness is adjusted to 10 to 30 µm is laminated on this nonwoven fabric, to attain a laminate sheet.

<Absorbent Body>

Any absorbent body 4 can be used provided that it can absorb and keep the liquid (the body fluid), however, those which are bulky, hard to deform and less chemically stimulant are desirable. Moreover, as absorbent body 4, pulp, chemical pulp, rayon, acetate rayon, natural cotton, the polymer absorbent body, the fiber polymer absorbent body, and synthetic fiber can used alone or by blending thereof. Additionally, foam material and cellulose foam material to which the hydrophilic treatment is applied can be used.

The absorbent body 4 is produced by making as air laid blended with polymer absorbent body, melt blown nonwoven fabric to which the hydrophilic treatment is applied, spun lace nonwoven fabric mainly composed of hydrophilic fiber, tissue, continuous foam to which the hydrophilic treatment is applied, cellulose foam, etc. At this time, the volume is adjusted properly by overlapping, and folding as necessary. Moreover, absorbent body 4 is not limited to the sheet shape, it may be used after crushing, and the form is not limited.

The absorbent body 4 is a fiber which chosen, for instance, within the range of 1 to 38 mm in the fiber length and, 1.1 to 3.3 dtex in fiber diameters, and concretely, it is produced by the following method. First, 3 to 30 weight % of branched rayon, and 70 to 97 weight % of the rayon are blended at this rate, and the specific weight by unit is adjusted to 20 to 40 g/m². This wet forming spun lace nonwoven fabric is adjusted to the dimension of 2 to 10 mm within the range of 100 to 500 g/m² in the overlapping specific weight per unit.

<Mini Sheet Piece>

It is preferable to use the one having the extensibility or the retractility at least for the transverse direction, though the material similar to the surface side sheet 2 and the back side sheet 3 mentioned above can be used as the mini sheet piece 5.

As the mini sheet piece expands at least in the width direction in proportion to the size of the finger, even if the size of the fingertip of the wearer is larger than the set finger insertion opening, by using such a material for the mini sheet piece 5, the interlabial product according to the present invention can surely be used, regardless of the size of the fingertip of the wearer.

Moreover, there are concretely films that are derived from the biodegradable materials such as polylactic acid, polybutyine succinate, the spun bond nonwoven fabric, the melt blown nonwoven fabric, etc. as a material used for the mini sheet piece 5. There are films, nonwoven fabrics, or the like that are derived from the water-soluble materials such as PVA and CMC, too. In addition, there are the water dissipating tissue, the spun lace nonwoven fabric, etc. mainly composed of the cellulose fiber, the regenerated cellulose fiber, and so on, too.

A material suitable for the mini sheet piece 5, is a spun lace nonwoven fabric blended with a necessary amount of fiber within the range of 1 to 38 mm in the fiber length, and preferably within the range of 2 to 20 mm, and within the range of 1.1 to 3.3 dtex in the fineness, and adjusted within the range of quantity of specific weight per unit 20 to 60 g/m², and as for the blending ratio of the fibril fiber and filament, it is 3 to 30 weight % of the fibril fiber, and 70 to 97 weight % of the filament.

A laminate sheet where the nonwoven fabric including the fibril fiber is stuck may be used for the spun bond nonwoven fabric and the melt blown nonwoven fabric mainly composed of biodegradable material. At this time, it is preferable to set the nonwoven fabric including the fibril fiber to the garment face side, in view of the wettability to the discharged water of the toilet, the mutual rubbing of mini sheet pieces, and so on.

<Adhesive>

As the adhesive used for bonding the surface side sheet 2, the absorbent body 4, the back side sheet 3, and the mini sheet piece 5 at the time of forming the interlabial product, the pressure-sensitive adhesive mainly composed of synthetic rubbers such as styrene-ethylene·butadiene-styrene block copolymer (SEBS), styrene-butadiene-styrene copolymer (SBS), styrene-isoprene-styrene block copolymers (SIS), the thermo-sensitive adhesive mainly composed of synthetic rubbers such as ethyl vinyl alcohol (EVA), and polyvinyl alcohol that has the water solubility or water bloating characteristic may be listed. And, these adhesives are spread in linear, spiral, atomized, $\Omega$, and others form. In addition, the embossing finish may be used for bonding in the combination with the above-mentioned adhesive, to make the shape as the product easy to be maintained, even in the wet state during the use. The emboss pattern for this may be dot, lattice, flat, and so on, without limiting to them.

[Composition of the Interlabial Product Folded in Two Parts]

The interlabial product 1, for instance, is folded in two parts and worn between labia and, at this time, the surface side sheet 2 on the body face side that is the outermost side stretches by the thickness of the absorbent body 4 even if the total size L in the transverse direction of the surface side sheet 2 in the folded state is same as the size L1 or slightly longer than the size L1 in the transverse direction of the surface side sheet 2 in the not-folded state. As a result, the point of the labia opens, and the interlabial product 1 might drop out, because a power to open the both sides edge of the folded interlabial product 1 works, even if it is made to wear between labia in the two-folded state.

Figure 4:
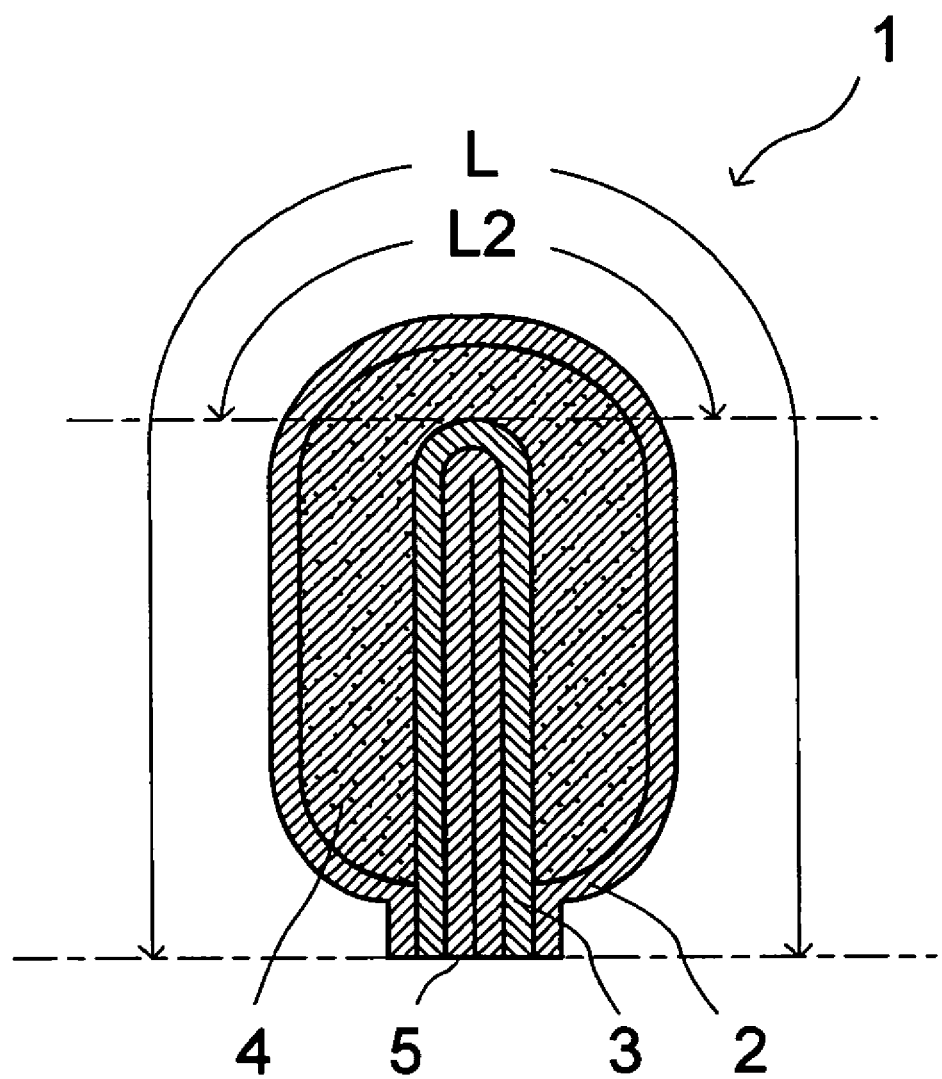
FIG. 4 is a cross-sectional view showing a state where the above-mentioned interlabial product is folded in two parts.

Then, the interlabial product 1 is folded in two parts, so that the back side sheet 3 come into contact each other along the centerline in the longitudinal direction, as shown in FIG. 4. Here, the total size L in the transverse direction of the surface side sheet 2 in the folded state is, at least, the sum of the apparent size L1 (Refer to FIG. 1B) in the transverse direction in the tabular state before folding it in two parts and the length L2 (the elongation length) that corresponded to the circumferential length of a semicircle taking the thickness of the interlabial product 1 in the state opened like the plane. As a result, the power for returning to the state before folding the interlabial product 1, namely, the power with which the both sides edge start opening can be controlled, by preventing the absorbent body 4 from pressing the surface side sheet 2. Therefore, there is no possibility of dropping out of the interlabial product 1, even if the interlabial product 1 is folded in two parts for wearing.

As a method for lengthening the total size in the transverse direction of the surface side sheet 2 than the size in the transverse direction in the tabular shape, the following method may be listed. For instance, there is a method for making the total size in the transverse direction of the surface side sheet larger than the total size in the transverse direction of the back side sheet, and bonding to the back side sheet 3 with the surface side sheet 2 loosened in the transverse direction. Moreover, there is also a method of bonding the surface side sheet 2 to the back side sheet 3 in the state where this back side sheet 3 and the absorbent body 4 are folded in two parts. There is also a method of making the surface side sheet 2 be easily extended in the transverse direction, and bonding the surface side sheet 2 and the back side sheet 3 in the tabular state. At this time, the ripple treatment may be applied to the surface side sheet 2 along the transverse direction, and the slit may be exerted, and moreover, the maximum elongation degree in the transverse direction may be made as 100% or more, as the characteristic of the surface side sheet itself.

Though the interlabial product 1 of this embodiment has the mini sheet piece 5 attached across two sides extending along the longitudinal direction of the interlabial product 1, on the garment face side of the back side sheet 3, it is not limited to this shape, for instance, you can wear the interlabial product by installing a projection on the face side (the garment face side) opposite to the body side, in place of the mini sheet piece 5, and picking this projection by two fingers. Furthermore, it may be the one that the mini sheet and the projection part are not installed at all.

[Sheet for Wrapping Used for the Wrapping Body of the Interlabial Product]

It is possible to discard the wrapping body to the flush toilet with the water-degradable interlabial product, by making the wrapping body that wraps the interlabial product water-degradable so that it will degrade in water, and consequently, the burden of wearing thereof can be removed. Therefore, it is preferable to make the sheet for wrapping the individual wrapping body to be water-degradable. The one used in the surface side sheet and the back side sheet mentioned above can be used as a material of such a sheet for wrapping. Concretely, natural fibers such as wood pulps including softwood pulps, hardwood pulps and so on, hemp, kenaves, linters pulps and so on may be enumerated. Regenerated celluloses such as rayon and acetate rayon, and synthetic fibers such as polypropylene, polyester, polyurethane, polyvinyl alcohol and so on may be enumerated. Moreover, biodegradability material contains the poly lactic acid fiber, the polybutylesuccinate fiber, the starch fiber, the carboxymethyl cellulose fiber, and so on. Among them, the one that is hydrophilic, and mainly composed of the rayon that can freely be selected within the range of 1 to 38 mm in the fiber length is preferable from the viewpoint of the affinity with the menstrual blood and the fitness with the inner wall of labia. As a result, a bridge structure having flexibility while preventing the filament being separated mutually, because the length of the branch hair can be lengthened as the fibril fiber, can be attained.

Besides, the sheet for wrapping is formed into melt blown, spun bond, point bond, through air, needle punch, wet paper, wet forming spun lace and so on, by blending the hydrophilic fiber where little hydrophilic surface active agent is deposited alone or the necessary amount.

The fibril fiber is attained by the formation of branch hairs like the outgrowth of hair in a way to tear the surface of the fiber, by beating of the aforementioned single fiber. This degree of beating is 600 cc or less, more preferably in the range of 100 to 400 cc. Besides, the fibril fiber is blended with the fiber that composes the sheet for wrapping at least at the rate of 2 weight %, and preferably within the range of 3 to 30 weight %. When the fibril fiber is fewer than 2 weight %, it is likely to degrade while wearing it, because the bridge structure is too little and the elongation degree in the wet state doesn't improve. On the other hand, the bridge structure increases too much, when the fibril fiber is more than 30 weight % and a flexible texture of the sheet for wrapping might be damaged.

It should be noted that as the fibril fiber, the rayon that is hydrophilic and excellent in the affinity with the menstrual blood and the fitness with the inner wall of labia, and moreover, that can be selected freely among those with long fiber length, is suitable. The rayon allows to attain the bridge structure having flexibility while preventing the filament being separated mutually, because the length of the branch hair can be lengthened, when it is fibrillated through beating, as it can be produced by the wet method or the dry method, and the fiber length can freely be selected within the range of 1 to 38 mm.

EXAMPLE

The examples of the surface side sheet blended the fibril fiber shall be described in comparison with the comparative examples, as for the property (the tensile strength) and the water dispersibility of the surface side sheet itself, and the practicability (the state on the surface under wearing) of the interlabial product that uses this surface side sheet.

Example 1

The surface side sheet was produced according to the following procedures. First of all, the rayon with 1.7 dtex in the fineness and 5 mm in the fiber length at the rate of 60 weight %, the fibrilrayon (the one that is 300 cc in beating) with 1.7 dtex in the fineness and 5 mm in the fiber length at the rate of 5 weight %, and the softwood pulp at the rate of 35 weight % are blended. Next, these blended fibers are laminated by a specific weight per unit of 40.5 g/m$^2$ and fibers are intertwined mutually by a water-flow of 160 kg/cm$^2$ total hydraulic pressure (corresponding value; 15.68 MN/m$^2$), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines for drying (the sheet is sent along a roll set to the temperature of 120° C. and an air set to the volume of air of 25 m/sec is jetted at 160° C.) to produce a wet forming spun lace nonwoven fabric whose density is adjusted to 0.134 g/cm$^3$ (corresponding value; 134 kg m$^3$).

Example 2

The surface side sheet was produced according to the following procedures. First of all, the rayon with 1.7 dtex in the fineness and 5 mm in the fiber length at the rate of 60 weight %, the rayon (the one that is 300 cc in beating) with 1.7 dtex in the fineness and 5 mm in the fiber length at the rate of 10 weight %, and the softwood pulp at the rate of 30 weight % are blended. Next, these blended fibers are laminated by a specific weight per unit of 39.5 g/m$^2$ and fibers are intertwined mutually by a water-flow of 160 kg/cm$^2$ total hydraulic pressure (corresponding value; 15.68 MN/m$^2$), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines (the sheet is sent along a roll set to the temperature of 120° C. and an air set to the volume of air of 25 m/sec is jetted at 160° C.) for drying, to produce a wet forming spun lace nonwoven fabric whose the density is adjusted to 0.138 g/cm$^3$ (corresponding value; 138 kg/m$^3$).

Example 3

The surface side sheet was produced according to the following procedures. First of all, the rayon with 1.7 dtex in the fineness and 5 mm in the fiber length at the rate of 60 weight %, the rayon (the one that is 300 cc in beating) with 1.7 dtex in the fineness and 5 mm in the fiber length at the rate of 15 weight %, and the softwood pulp at the rate of 25 weight % are blended. Next, these blended fibers are laminated by a specific weight per unit of 41.3 g/m$^2$ and fibers are intertwined mutually by a water-flow of 160 kg/cm$^2$ total hydraulic pressure (corresponding value; 15.68 MN/m$^2$), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines (the sheet is sent along a roll set to the temperature of 120° C. and an air set to the volume of air of 25 m/sec is jetted at 160° C.) for drying, to produce a wet forming spun lace nonwoven fabric whose the density is adjusted to 0.140 g/cm$^3$ (corresponding value; 140 kg/m$^3$).

Example 4

The surface side sheet was produced according to the following procedures. First of all, the rayon with 1.7 dtex in the fineness and 5 mm in the fiber length at the rate of 60 weight %, the rayon (the one that is 300 cc in beating) with 1.7 dtex in the fineness and 5 mm in the fiber length at the rate of 20 weight %, and the softwood pulp at the rate of 20 weight % are blended. Next, these blended fibers are laminated by a specific weight per unit of 40.1 g/m² and fibers are intertwined mutually by a water-flow of 160 kg/cm² total hydraulic pressure (corresponding value; 15.68 MN/m²), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines (the sheet is sent along a roll set to the temperature of 120° C. and an air set to the volume of air of 25 m/sec is jetted at 160° C.) for drying, to produce a wet forming spun lace nonwoven fabric whose the density is adjusted to 0.142 g/cm³ (corresponding value; 142 kg/m³).

COMPARATIVE EXAMPLE

A surface side sheet where the fibril fiber produced by beating rayon with 600 cc was blended, and a surface side sheet where the fibril fiber was not blended were used as the comparative example.

Comparative Example 1

The surface side sheet was produced according to the following procedures. First of all, the rayon with 1.7 dtex in the fineness and 5 mm in the fiber length at the rate of 60 weight %, the fibrilrayon (the one that is 600 cc in beating) with 1.7 dtex in the fineness and 5 mm in the fiber length at the rate of 15 weight %, and the softwood pulp at the rate of 25 weight % are blended. Next, these blended fibers are laminated by a specific weight per unit of 41.6 g/m² and fibers are intertwined mutually by a water-flow of 160 kg/cm² total hydraulic pressure (corresponding value; 15.68 MN/m²), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines (the sheet is sent along a roll set to the temperature of 120° C. and an air set to the volume of air of 25 m/sec is jetted at 160° C.) for drying, to produce a wet forming spun lace nonwoven fabric whose the density is adjusted to 0.136 g/cm³ (corresponding value; 136 kg/m³).

Comparative Example 2

The surface side sheet was produced according to the following procedures. First of all, the rayon with 1.7 dtex in the fineness and 5 mm in the fiber length at the rate of 60 weight %, the fibrilrayon (the one that is 600 cc in beating) with 1.7 dtex in the fineness and 5 mm in the fiber length at the rate of 30 weight %, and the softwood pulp at the rate of 10 weight % are blended. Next, these blended fibers are laminated by a specific weight per unit of 40.8 g/m² and fibers are intertwined mutually by a water-flow of 160 kg/cm² total hydraulic pressure (corresponding value; 15.68 MN/m²), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines (the sheet is sent along a roll set to the temperature of 120° C. and an air set to the volume of air of 25 m/sec is jetted at 160° C.) for drying, to produce a wet forming spun lace nonwoven fabric whose the density is adjusted to 0.138 g/cm³ (corresponding value; 138 kg/m³).

Comparative Example 3

The surface side sheet was produced according to the following procedures. First of all, the rayon with 1.7 dtex in the fineness and 5 mm in the fiber length at the rate of 60 weight %, and the softwood pulp at the rate of 40 weight % are blended. Next, these blended fibers are laminated by a specific weight per unit of 39.4 g/m² and fibers are intertwined mutually by a water-flow of 160 kg/cm² total hydraulic pressure (corresponding value; 15.68 MN/m²), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines (the sheet is sent along a roll set to the temperature of 120° C. and an air set to the volume of air of 25 m/sec is jetted at 160° C.) for drying, to produce a wet forming spun lace nonwoven fabric whose the density is adjusted to 0.147 g/cm³ (corresponding value; 147 kg/m³).

Comparative Example 4

The surface side sheet was produced according to the following procedures. First of all, rayon with 2.2 dtex in the fineness and 51 mm in the fiber length is laminated by a specific weight per unit of 40.5 g/m² and intertwined mutually by a water-flow of 140 kg/cm² total hydraulic pressure (corresponding value; 13.72 MN/m²), 2000 cc/cm·min total water-flow quantity (corresponding value; 2.000 l/cm·min) from 3 lines of nozzles (nozzle diameter 92 μm and nozzle pitch 0.5 mm) disposed in parallel to make a sheet, while transferring this fiber laminated body by 70 m/min. Following this, this fiber transformed into a sheet is dried by sending an air flow set to the temperature of 110° C., 2 m/sec by a rate of 70 m/min, to produce a dry forming spun lace nonwoven fabric whose the density is adjusted to 0.081 g/cm³ (corresponding value; 81 kg/m³).

<1. Property (Tensile Strength) of the Surface Side Sheet>

The tensile strength was measured for the examples 1 to 4 of the surface side sheet that comprises the filament and the fibril fiber with branch hairs formed by the degree of beating of 300 cc, the surface side sheet made of the fiber blended with the fibril fiber having branch hairs formed by a degree of beating of 600 cc and the comparative examples 1 to 3 of the fiber surface side sheet not blended with the fibril fiber. Concretely, the test piece was cut out vertically or horizontally by the width of 25 mm and measured by a Tensilon tensile test machine (RTA-100, made by Orientec Co., Ltd.) with chuck distance of 50 mm and at the speed of 100 mm/min (corresponding value; 6 m/h).

Note that, in wet, the tensile strength was measured by the following procedures. First of all, the test piece was weighed in advance, and the artificial menstrual blood described below was jetted in mist by spreading all over the test piece until attaining 500% of its weight. Afterwards, this test piece was coated with a liquid impermeability material, and left for one minute under the environment of 20° C. and 60% in humidity, and then it was examined. Table 1 shows the results thereof.

TABLE 1

Property of the surface side sheet

|  |  |  | Example 1 | Example 2 | Example 3 | Example 4 | Comparative example 1 | Comparative example 2 | Comparative example 3 |
|---|---|---|---|---|---|---|---|---|---|
| Production method |  |  | Wet forming spun lace | Wet forming spun lace | Wet forming spun lace | Wet forming spun lace | Wet forming spun lace | Wet forming spun lace | Wet forming spun lace |
| Rayon (1.7dtex 5 mm) |  |  | 60 | 60 | 60 | 60 | 60 | 60 | 60 |
| Fiblilrayon (1.7dtex 5 mmk, beating 600 cc) |  |  |  |  |  |  |  | 15 | 30 |
| Fiblilrayon (1.7dtex 5 mm, beating 300 cc) |  |  | 5 | 10 | 15 | 20 |  |  |  |
| Softwood pulp |  |  | 35 | 30 | 25 | 20 | 25 | 10 | 40 |
| By a specific weight per unit |  | g/m² | 40.5 | 39.6 | 41.3 | 40.1 | 41.6 | 40.8 | 39.4 |
| Density |  | g/cm³ | 0.134 | 0.138 | 0.14 | 0.142 | 0.136 | 0.138 | 0.147 |
| On Dry | Longitudinal maximun tensile strength | cN/25 mm | 1490 | 1390 | 1105 | 986 | 1113 | 1520 | 1489 |
|  | Longitudinal maximum tensile elongation degree | % | 15.5 | 16.2 | 16.9 | 14.8 | 12.6 | 15.8 | 16.1 |
| On Wet | Longitudinal maximun tensile strength on 500% wet | cN/25 mm | 190 | 214 | 187 | 197 | 110 | 91 | 101 |
|  | Longitudinal maximum tensile elongation degree on 500% wet | % | 26.3 | 27.3 | 34.3 | 33.9 | 8.1 | 9.5 | 7.8 |
| On Dry | Longitudinal maximun tensile strength | cN/25 mm | 1390 | 1081 | 876 | 888 | 976 | 1210 | 1181 |
|  | Longitudinal maximum tensile elongation degree | % | 12.9 | 18.4 | 15.1 | 12.6 | 10.1 | 13.5 | 14.6 |
| On Wet | Longitudinal maximun tensile strength on 500% wet | cN/25 mm | 156 | 166 | 169 | 158 | 89 | 144 | 151 |
|  | Longitudinal maximum tensile elongation degree on 500% wet | % | 25.4 | 26.4 | 29.7 | 31.3 | 9.0 | 8.9 | 10.1 |

As the result, it was observed that the elongation degree after fracture increases in wet of 500% than in dry, for the examples 1 to 4 of blending the fibril fiber beaten with 300 cc. Moreover, it was also observed that, when the ratio of the fibril fiber increases, the elongation degree after fracture in wet of 500% increases. On the other hand, an increase in the elongation degree after fracture in wet of 500% was not observed in the comparative examples 1, 2 of the blending the fibril fiber beaten with 600 cc and the comparative example 3 of not blending the fibril fiber. Moreover, the elongation degree after fracture in wet of 500% was low as 10% or less and easy to break.

Thus, for the examples 1 to 4, in the wet state after having the absorbed body fluid such as the menstrual blood and so on, the elongation degree increases more than in the dry state, and moreover, the tensile strength also increases compared with the case not blended with the fibril fiber, allowing to confirm the stability of the wet state.

It should be noted that the artificial menstrual blood in the present invention means a liquid adjusted according to the following procedures. Sodium carboxylmethylcellulose (NaCMC) of 8 g are added little by little while stirring into glycerin of 80 g, for prepare a solution 1. Next, the solution 1 prepared previously is added little by little while stirring by an agitator to one liter, of ion exchange water. After the solution 1 is added, sodium chloride (NaCl) of 10 g and sodium hydrogen carbonate ($NaHCO_3$) are added little by little, stirred and dispersed (stirred for three hours at the max rotation by the agitator LABO-STIRRER L-35 made by Yamato Co., Ltd.). For all of the aforementioned reagents, Wako 1st class reagents shall be used. Next, food dyes (made by KOYO Produc Co., Ltd.): the red No. 102 of 8 g, the red No. 2 of 2 g, the yellow No. 5 of 2 g are added for one liter of ion exchange water and stirred (stirred for one hour at the max rotation by the agitator LABO-STIRRER L-35 made by Yamato Co., Ltd.), and the viscosity measured by a viscosity finder (VISMETRON) made by Sibaura System Co., Ltd.) is assumed to be 22 to 26 mPa·s.

<2. Water Dispersibility of the Surface Side Sheet>

As for the water dispersibility of the surface side sheet of the examples 1 to 4, the time for the surface side sheet to be dispersed in water like fragments and not to maintain the original shape any more was tested by the water degradation test described below, comparing with the surface sheet of the comparative example 4. Table 2 shows the result thereof.

TABLE 2

Water dispersibility of the surface side sheet

|  | Example 1 | Example 2 | Example 3 | Example 4 | Comparative example 4 |
|---|---|---|---|---|---|
| Production Method | Wet forming spun lace | Wet forming spun lace | Wet forming spun lace | Wet forming spun lace | Wet forming spun lace |
| Rayon (1.7dtex 5 mm) | 60 | 60 | 60 | 60 |  |
| Fiblilrayon (1.7dtex 5 mm, beating 600 cc) |  |  |  |  |  |

TABLE 2-continued

Water dispersibility of the surface side sheet

|  |  | Example 1 | Example 2 | Example 3 | Example 4 | Comparative example 4 |
|---|---|---|---|---|---|---|
| Fiblilrayon (1.7dtex 5 mm, beating 300 cc) |  | 5 | 10 | 15 | 20 |  |
| Softwood pulp |  | 35 | 30 | 25 | 20 |  |
| Rayon (2.2dtex 5 mm) |  |  |  |  |  | 100 |
| By a specific weight per unit | g/m$^2$ | 40.5 | 39.6 | 41.3 | 40.1 | 25.0 |
| Density | g/cm$^3$ | 0.134 | 0.138 | 0.14 | 0.142 | 0.081 |
| Water degradation rate | sec | 39 | 28 | 41 | 35 | incapable measurement |

In the examples 1 to 4, the surface side sheet was dispersed within about 40 seconds and the original shape of the sheet was not maintained, thus allowing to confirm such a water degradability that it can be discarded into the toilet.

Besides, the water degradability was examined according to the following procedures. The test piece is made by preparing the surface side sheet to 100 mm×100 mm and the test piece formed like the parachute is introduced into water from the sharp tip thereof, while stirring 300 ml of water in a cylindrical container by the speed of rotation 600 rpm by a magnetic stirrer (Torcon stirrer MM-ST with speed meter made by Mitamura Manufacturing Co., Ltd.). Then, the time until a wad of the fiber disappears is measured. The chip that is used for stirring is a disk of 35 mm in diameter, and 12 mm in height.

<3. Practicability of the Interlabial Product that Uses the Surface Side Sheet_(the State on the Surface Under Wearing)>

For the examples 1 to 4 of the surface side sheet that comprises the filament and the fibril fiber with branch hairs formed by the degree of beating of 300 cc, the surface side sheet made of the fiber blended with the fibril fiber having branch hairs formed by a degree of beating of 600 cc and the comparative examples 1 to 3 of the fiber surface side sheet not blended with the fibril fiber, the menstrual blood absorption quantity in the interlabial product and the state on the surface after it has been worn were confirmed, as following that the interlabial product was formed using respective surface sheets, to be worn for about two hours by ten women on the second day of the menstruation. In wearing it, it was worn together with a napkin made by Uni-Charm Corporation, the brand name "Sofy Sara fin (the registered trademark)". Table 3 shows the results of the examination.

It was confirmed that there was no evil in use, though little fuzz was observed in the example 1. In the examples 2 to 4, it was confirmed the original shape has been conserved almost completely without damage. On the other hand, for the comparative examples 1, 2, it was torn, and the fiber from the surface side sheet remained inside the body. Moreover, it was confirmed that it was torn, though the fiber did not remain inside the body, for the comparative example 3.

Figure 5:
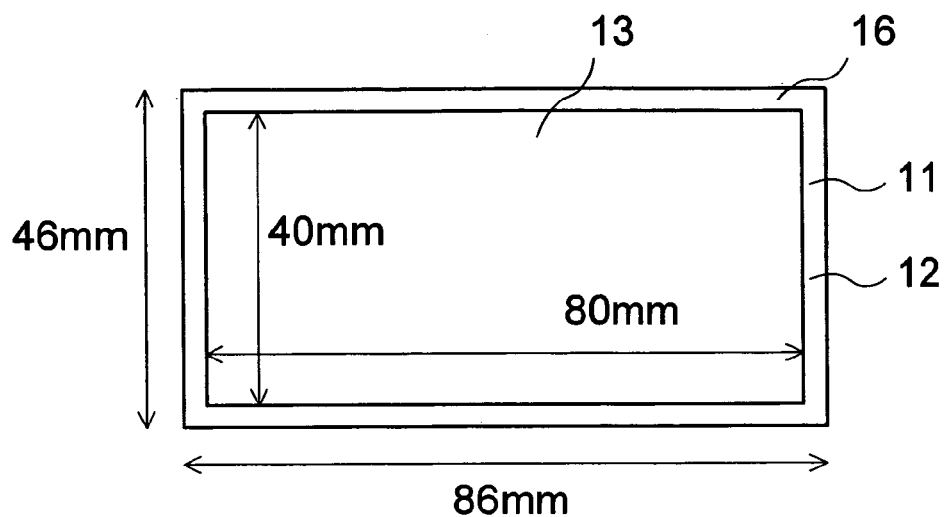
Figure 5:
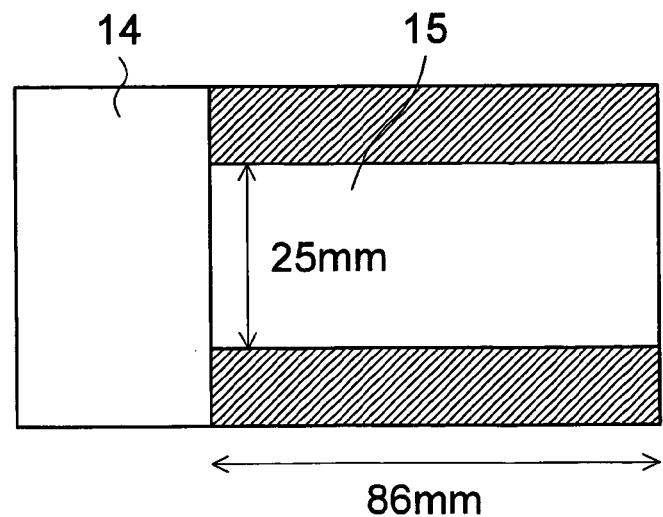

As for the interlabial product used for the above-mentioned examination, it concerns the one having the rectangle shape of 46 mm in width×86 mm in length as shown in FIG. 5 composed of a surface side sheet, an absorbent body, a back side sheet, and a mini sheet piece overlaid in this order and a flap part composed of a surface side sheet, a back side sheet, and a mini sheet piece is formed with the width of 3 mm outside the edge part thereof.

The above-mentioned interlabial product is, concretely, the one produced according to the following procedures. The absorbent body has a size of 40 mm wide×80 mm long, pulp flocculated by a pulp crusher and laminated by a specific weight per unit of 250 g/m$^2$ and pressed to the thickness of 6 mm. The back side sheet is a nonwoven fabric of water-soluble paper of 18 g/m$^2$ in a specific weight per unit, laminated to the thickness of 20 μm with polybutylenesuccinate resin. The mini sheet piece is a film of 20 μm in the thickness that is formed with polybutylenesuccinate resin. First, the thermo-sensitive type pot melt of which the principal ingredient is SEBS is applied in spiral by the weight of 3 g/m$^2$ in a specific weight per unit over an area of 5 mm in width, 40 mm in length on the body side of the back side sheet, and the absorbent body is overlapped. Next, the surface side sheet is placed on the body side of the

TABLE 3

State on the surface of interlabial product by surface side sheet after it has been worn

|  |  | Example 1 | Example 2 | Example 3 | Example 4 | Comparative example 1 | Comparative example 2 | Comparative example 3 |
|---|---|---|---|---|---|---|---|---|
| Duration of wearing | min | 120 | 105 | 130 | 120 | 130 | 100 | 120 |
| Menstrual blood absorption quantity in the interlabial product | g | 5.4 | 4.4 | 3.3 | 5.1 | 3.8 | 2.9 | 4.0 |
| State on the surface |  | ○ | ⊚ | ⊚ | ⊚ | XX | XX | X |

Estimation
⊚ Original shape conserved almost completely without damage
○ A little fuzz observed with no evil in use,
X Torn but not remained inside the body
XX Torn and remained inside the body absorbent body, and the surrounding of the absorbent body is heat-sealed by the embossing finish of 2 mm in width, the surface side sheet and the back side sheet are bonded mutually, to seal thereby the absorbent body. Following this, the mini sheet piece is arranged over the length of 60 mm from the edge of the interlabial product on the garment face side of the back side sheet, and a breadth that allows inserting the finger between the mini sheet piece and the back side sheets, is formed. Next, the both side parts of the mini sheet piece and the back side sheet are bonded with the hot melt of which the principal ingredient is SEBS, so that the width of this breadth may become 25 mm.

<4. Water Dispersibility of the Interlabial Product>

Figure 6:
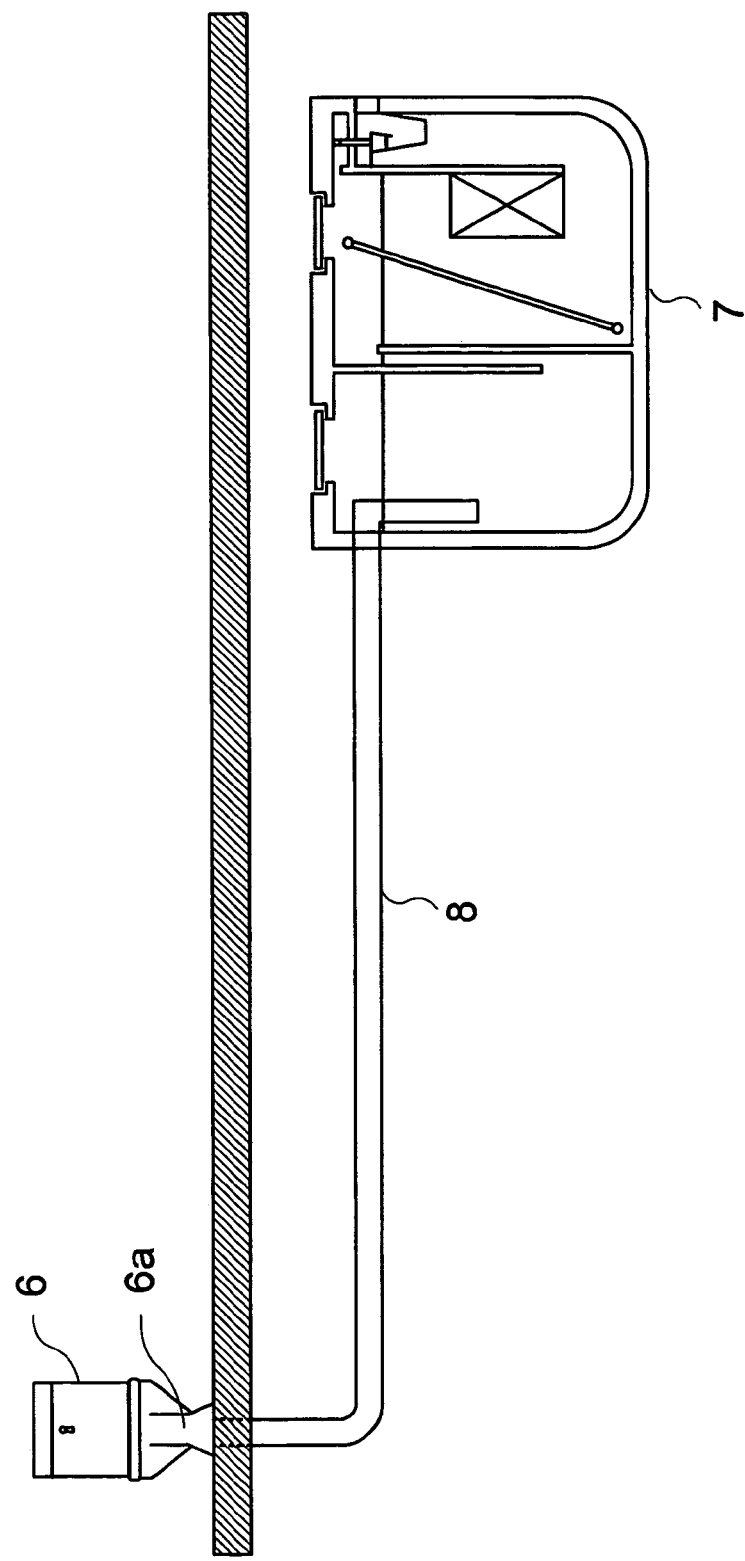
FIG. 6 is a schematic diagram of the flush lavatory used to examine the aqueous dispersibility of the above-mentioned interlabial product.

The water dispersibility in throwing into the toilet was examined by discarding the interlabial product using each surface side sheet to the flush toilet shown in FIG. 6, and confirming the degraded situation of the interlabial product thereafter by watching with eyes, for the examples 1 to 4 and the comparative example 4 of the surface side sheet. Note that the composition of the interlabial product using each surface side sheet was assumed to be the same as those explained in the above-mentioned <3. Practicability of the interlabial product that uses the surface side sheet>.

As a result, the interlabial product that uses the surface side sheet of examples 1 to 4 and the comparative example 4 flowed without being blocked in the distributing pipe by a single flush, and reached the septic tank. Afterwards, the interlabial product that uses the surface side sheet of the examples 1 to 4 began to untie the mutual twining of fibers that compose the surface side sheet from about the third day in contact with a large amount of water, and the surface side sheet was dispersed in fragments on the fourth day, secede the absorbent body arranged on the back side of the surface side sheet, and the original shape of the interlabial product was completely lost. On the other hand, the interlabial product that uses the surface side sheet of the comparative example 4 did not untie the mutual twining of fibers that composes the surface side sheet even in contact with a large amount of water, and the original shape of the interlabial product was kept.

Thus, as the interlabial product that uses the surface side sheet of the examples 1 to 4 degrades gradually from the surface side sheet after it was discarded to the septic tank, disperses, and loses the original shape of the interlabial product, it was confirmed that even the check trader of the septic tank was not able to recognize the product after use, and it was excellent for the public health.

The flush toilet used for the examination is composed of a European style toilet 6 of the semi-siphon type that has a trap part 6a, a septic tank 7, and piping 8 that connects these European style toilet 6 and the septic tank 7, as shown in FIG. 6. In this flush toilet, the displacement of a single flush is eight liters. The diameter of the trap part 6a of the European style toilet 6 is 53 mm. Piping 8 is 100 mm in diameter, 1/100 in gradient, and 10 m in length. Septic tank 7 is a single processing septic tank filled only with tap water.

For this examination, the toilet paper was cut out by 2 m, when the interlabial product was thrown into the toilet; this cut out toilet paper was divided into substantially equal three pieces, and each of these three pieces were rounded moderately, and thrown into the discharge hole. Afterwards, the interlabial product was thrown into the discharge hole, the discharged water was poured, and it was drained out. Toilet paper was used by overlapping two water soluble tissues of 14 mm in width and 18 g/m² in a specific weight per unit.

The reason to discard the interlabial product with toilet paper is that it is a common practice for women wearing the interlabial product to wipe off the menstrual blood attached to the labia by using toilet paper, after the interlabial product has been used, besides the time when they do their needs. Moreover, the length of toilet paper was assumed to be 2 m, because the average amount of use of toilet paper per time by women is about 2 m.

Next, the example that uses the fiber sheet including the fibril fiber for the wrapping body that wraps the water degradable interlabial product shall be described as for the property of the sheet for wrapping itself (the tensile strength) and the water dispersibility, in comparison with the comparative example using the fiber sheet not including the fibril fiber.

Example 5

The sheet for wrapping was produced according to the following procedures. First of all, the rayon with 1.7 dtex in the fineness and 5 mm in the fiber length at the rate of 40 weight %, the fibrilrayon (the one that is 300 cc in beating) with 1.7 dtex in the fineness and 5 mm in the fiber length at the rate of 15 weight %, and the softwood pulp at the rate of 45 weight % are blended. Next, these blended fibers are laminated by a specific weight per unit of 30.3 g/m² and fibers are intertwined mutually by a water-flow of 160 kg/cm² total hydraulic pressure (corresponding value; 15.68 MN/m²), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines (the sheet is sent along a roll set to the temperature of 120° C. and an air set to the volume of air of 25 m/sec is jetted at 160° C.) for drying, to produce a wet forming spun lace nonwoven fabric whose the density is adjusted to 0.140 g/cm³ (corresponding value; 140 kg m³).

Example 6

The sheet for wrapping was produced according to the following procedures. First of all, the rayon with 1.7 dtex in the fineness and 5 mm in the fiber length at the rate of 50 weight %, the fibrilrayon (the one that is 300 cc in beating) with 1.7 dtex in the fineness and 5 mm in the fiber length at the rate of 20 weight %, and the softwood pulp at the rate of 30 weight % are blended. Next, these blended fibers are laminated by a specific weight per unit of 31.5 g/m² and fibers are intertwined mutually by a water-flow of 160 kg/cm² total hydraulic pressure (corresponding value; 15.68 MN/m²), 1680 cc/cm·min total water-flow quantity (corresponding value; 1.68 l/cm·min) from two lines of nozzles (nozzle diameter 92 μm and nozzle pitch 0.5 mm) disposed in parallel to make a sheet. Following this, these fibers transformed into a sheet pass through the dry process of two parallel lines for drying (the sheet is sent along a roll set to the temperature of 120° C. and an air set to the volume of air of 25 m/sec is jetted at 160° C.) to produce a wet forming spun lace nonwoven fabric whose the density is adjusted to 0.142 g/cm³ (corresponding value; 142 kg m³).

Comparative Example 5

The sheet for wrapping was produced according to the following procedures. First of all, rayon with 2.2 dtex in the fineness and 38 mm in the fiber length is laminated by a specific weight per unit of 29.4 g/m² and intertwined mutually by a water-flow of 140 kg/cm² total hydraulic pressure (corresponding value; 13.72 MN/m²), 2000 cc/cm·min total water-flow quantity (corresponding value; 2.000 l/cm·min) from 3 lines of nozzles (nozzle diameter 92 µm and nozzle pitch 0.5 mm) disposed in parallel to make a sheet, while transferring this fiber laminated body by 70 m/min. Following this, this fiber transformed into a sheet is dried by sending an air flow set to the temperature of 110° C., 2 m/sec by a rate of 70 m/min, to produce a dry forming spun lace nonwoven fabric whose the density is adjusted to 0.100 g/cm³ (corresponding value; 100 kg/m³).

<5. Property (Tensile Strength Characteristic) and Water Dispersibility of the Sheet for Wrapping>

The examination was performed by a method similar to the examination of the aforementioned <1. Property (the tensile strength)> and <2. Water dispersibility of the surface sheet> for the examples 5, 6 of the sheet for wrapping that comprises the filament and the fibril fiber where branch hairs are formed and the comparative example 5 of the sheet for wrapping comprising the fiber not blended with the fibril fiber. Table 4 shows the results thereof.

was able to be confirmed. Moreover, it was also confirmed to have the water degradability suitable for discarding in the toilet.

Note that, though the rayon, the fibrilrayon, and the softwood pulp were combined and used as the fiber that composes the surface side sheet and the sheet for wrapping in this example, the combination is not limited to this, but arbitrary ones among the aforementioned hydrophilic fibers may be combined, and used, or you may also use one of these hydrophilic fibers.

According to the present invention, the surface side sheet used for the interlabial product is made of hydrophilic fiber composed of filament and the fibril fiber provided with branch hairs branching from the surface, and at least a part of the branch hairs is made in a bridge structure where the filament and the fibril fiber bridge mutually. As a result, it doesn't become a problem in wearing, because the fiber doesn't easily get untied mutually, in the wet state with the absorbed body fluid such as the menstrual blood, as the uniting power between fibers can be improved, and it doesn't break while wearing it. On the other hand, it is possible to throw it into the flush toilet as it is, and the

TABLE 4

Property and water dispersibility of the sheet for wrapping

| | | Example 5 | Example 6 | Comparative example 5 |
|---|---|---|---|---|
| Production method | | Wet forming spun lace | Wet forming spun lace | Wet forming spun lace |
| Rayon (1.7dtex 5 mm) | | 40 | 50 | |
| Fiblilrayon (1.7dtex 5 mm, beating 600 cc) | | | | |
| Fiblilrayon (1.7dtex 5 mm, beating 300 cc) | | 15 | 20 | |
| Softwood pulp | | 45 | 30 | |
| Rayon (2.2dtex 5 mm) | | | | 100 |
| By a specific weight per unit | g/m² | 30.3 | 31.5 | 29.4 |
| Density | g/cm³ | 0.140 | 0.142 | 0.100 |
| On Dry Longitudinal maximun tensile strength | cN/25 mm | 832 | 769 | 1762 |
| Longitudinal maximum tensile elongation degree | % | 11.3 | 14.8 | 22.2 |
| On Wet Longitudinal maximum tensile strength on 500% wet | cN/25 mm | 112 | 89 | 1501 |
| Longitudinal maximum tensile elongation degree on 500% wet | % | 24.8 | 29.0 | 19.3 |
| On Dry Longitudinal maximun tensile strength | cN/25 mm | 667 | 703 | 576 |
| Longitudinal maximum tensile elongation degree | % | 10.2 | 11.6 | 10.1 |
| On Wet Longitudinal maximun tensile strength on 500% wet | cN/25 mm | 11.1 | 130 | 482 |
| Longitudinal maximum tensile elongation degree on 500% wet | % | 30.1 | 26.2 | 87.2 |
| Water degradation rate | sec | 29 | 22 | incapable measurement |

As a result, it was recognized that, when it was wet, the elongation degree after fracture increased more than when it was dry, and the elongation degree after fracture in the wet state increased when the ratio of the fibril fiber increased, in the examples 5, 6 that used the sheet for wrapping blended the fibril fiber. On the other hand, an increase in the elongation degree after fracture when it was wet was not observed in the comparative example 5 without a fibril fiber. Moreover, the sheet for wrapping disperses in water within about 30 seconds, and loses its original shape, and it was able to be confirmed to have the water degradability suitable for discarding in the toilet in the examples 5, 6.

Thus, for the examples 5, 6 also, similarly to the surface side sheet, in the wet state after having absorbed the menstrual blood or other body fluids, the elongation degree increases more than in the dry state, and moreover, the elongation strength also increases compared with the case not blended the fibril fiber, and the stability in the wet state burden of the waste disposal and so on after use can be removed, because this bridge structure decomposes gradually, and degrades to a degree to lose the original shape as the sheet, against a large amount of water, such as the running water of the toilet and so on.

Moreover, the hand does not get dirty, because it becomes unnecessary to handle with hands the interlabial product that has absorbed the body fluid such as the menstrual blood after use, as it can be thrown into the toilet as it is. Therefore, when a new interlabial product is to be worn, it is sanitary because the interlabial product will not be soiled.

Moreover, it degrades gradually from the surface side sheet, disperses in the water, and loses the original shape of the interlabial product, even if it is thrown into the flush toilet as it is after the interlabial product is used, and consequently, even the check trader of the septic tank cannot recognize the product after use visually, and moreover, it is also excellent for the public health.

Even if the interlabial product is thrown from the back side sheet to the toilet, the hydrophilic sheet installed on the garment face side of the back side sheet has the affinity immediately, by arranging the hydrophilic fiber sheet including the fibril fiber on the clothes side of the back side sheet which is liquid impermeable. Therefore, it is possible to discard it surely with the discharged water, by preventing the interlabial product from coming to the surface of the water. Moreover, the back side sheets might rub mutually when the interlabial product is worn, and the back side sheet of the interlabial product and the sanitary napkin might rub when the napkin is used together with the interlabial product. Even for such a case, as the friction is decreased by the back side sheet, the leak of the menstrual blood can be prevented from being caused as the back side sheet is untied. In addition, even if the back side sheet is soaked with the menstrual blood and it is wet, as the hydrophilic fiber sheet contains the fibril fiber, the bridge structure of this fibril fiber can decrease the breakage of the back side sheet further.

Moreover, as the surface side sheet according to the present invention and the interlabial product that uses this surface side sheet are not those achieving the water degradability by the composition of the resin, itchy, rough skin or other symptoms are not caused by the component eluded from the resin.

Besides, as the individual wrapping body wrapping the interlabial product, is composed by containing the fibril fiber similarly to the surface side sheet, the individual wrapping body becomes water degradable and, consequently, it is possible to discard it into the flush toilet as it is, and the burden of separate disposal of the wrapping body after opening the seal can be removed.

What is claimed is:

1. A water degradable surface side sheet for an interlabial product to be worn between labia, comprising:
    hydrophilic fibers in the range of 1 to 38 mm in length and fibril fibers having branch hairs branching from a surface; and
    bridge structures formed by forming bridges of the branch hairs between the hydrophilic fibers and the fibril fibers;
    wherein the fibril fibers are blended with the hydrophilic fibers, the fibril fibers representing between 3 and 30 weight percent of the blend.

2. The water degradable surface side sheet for the interlabial product according to claim 1,
    wherein the bridge structures improve stability of the hydrophilic fibers that are soaked in a small quantity of water, and the bridge structures are gradually dissolved in a large amount of water.

3. The water degradable surface side sheet for the interlabial product according to claim 1, wherein a maximum elongation degree of the sheet when wet is greater than a maximum elongation degree of the sheet when dry.

4. The water degradable surface side sheet for the interlabial product according to claim 1, wherein a degree of beating of the branch hairs of the fibril fibers is 100 cc to 400 cc.

5. The water degradable surface side sheet for the interlabial product according to claim 1, wherein the fibril fibers comprise rayon.

6. An interlabial product to be worn between labia, comprising:
    a water degradable surface side sheet facing the labia and a back side sheet arranged on an opposite side of the water degradable surface side sheet, the opposite side being a garment side,
    wherein the water degradable surface side sheet comprises hydrophilic fibers in the range of 1 to 38 mm in length and fibril fibers having branch hairs branching from a surface, wherein at least some of the branch hairs make bridges between the hydrophilic fibers and the fibril fibers.

7. The interlabial product according to claim 6, wherein a length of the surface side sheet in a transverse direction when the interlabial product is folded along a longitudinal fold line so that the water degradable surface side sheet is exposed, is greater than a length of the surface side sheet in the transverse direction when the interlabial product is tabular.

8. The interlabial product according to claim 6, wherein the back side sheet comprises a hydrophilic fiber including a fibril fiber.

9. The interlabial product according to claim 6, comprising a mini sheet piece for inserting a finger, wherein the mini sheet piece is provided on the back side sheet and includes a fibril fiber.

10. The interlabial product according to claim 6, wherein the interlabial product is for incontinence.

11. The interlabial product according to claim 6, wherein the interlabial product is for absorbing vaginal discharge.

12. A wrapping body having an interlabial product to be worn between labia and a wrapping sheet for enveloping the interlabial product,
    wherein the interlabial product comprises a water degradable surface side sheet facing the labia and a back side sheet arranged on a opposite side of the degradable surface side sheet, the opposite side being a garment side,
    wherein the water degradable surface side sheet comprises a hydrophilic fibers in the range of 1 to 38 mm in length and fibril fibers having branch hairs branching from its surface, wherein at least some of the branch hairs make bridges between the hydrophilic fibers and the fibril fibers, and
    the wrapping sheet includes fibril fibers.

13. A fibril fiber for a water degradable product, comprising branch hairs branching from a surface of the fibril fiber.

14. A method for improving a stability of a hydrophilic fiber soaked in small quantity of water, wherein the hydrophilic fiber comprises a fiber in the range of 1 to 38 mm in length and a fibril fiber having branch hairs branching from a surface, comprising the step of:
    making bridges between the fiber and the fibril fiber formed by at least some of the branch hairs.

* * * * *